United States Patent
Oguni et al.

(10) Patent No.: US 12,333,859 B2
(45) Date of Patent: Jun. 17, 2025

(54) INFORMATION PROCESSOR PERFORMING ARITHMETIC OPERATION USING MACHINE LEARNING

(71) Applicant: SEMICONDUCTOR ENERGY LABORATORY CO., LTD., Atsugi (JP)

(72) Inventors: Teppei Oguni, Kanagawa (JP); Tatsuya Okano, Kanagawa (JP); Kengo Akimoto, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 390 days.

(21) Appl. No.: 17/638,359

(22) PCT Filed: Aug. 25, 2020

(86) PCT No.: PCT/IB2020/057918
§ 371 (c)(1),
(2) Date: Feb. 25, 2022

(87) PCT Pub. No.: WO2021/044249
PCT Pub. Date: Mar. 11, 2021

(65) Prior Publication Data
US 2022/0292880 A1    Sep. 15, 2022

(30) Foreign Application Priority Data

Sep. 6, 2019 (JP) ................................. 2019-162687

(51) Int. Cl.
*G06V 40/16* (2022.01)
*G06N 3/08* (2023.01)
(Continued)

(52) U.S. Cl.
CPC ............. *G06V 40/176* (2022.01); *G06N 3/08* (2013.01); *G06T 7/62* (2017.01); *G06V 40/193* (2022.01); *G06T 2207/30201* (2013.01)

(58) Field of Classification Search
CPC ...... G06V 40/176; G06V 40/193; G06N 3/08; G06N 3/045; G06T 7/62;
(Continued)

(56) References Cited

U.S. PATENT DOCUMENTS 9,331,100 B2    5/2016   Yamazaki
10,959,615 B2   3/2021   Fujikado. et al.
(Continued)

FOREIGN PATENT DOCUMENTS

CN    104013414 A    9/2014
CN    105354985 A    2/2016
(Continued)

OTHER PUBLICATIONS

English Machine Translation of JP 2012-073876-A (Takagi, Published Apr. 12, 2012) (Year: 2012).*
(Continued)

*Primary Examiner* — Juan M Guillermety
(74) *Attorney, Agent, or Firm* — Fish & Richardson P.C.

(57) ABSTRACT

An information processing system is provided. The information processing system includes first and second information processors. The first information processor obtains a first moving image including a face and detecting an eye from two or more first images among the first moving image. The first information processor detects a pupil from the eye detected from the first image, calculating its size, and performing learning using a change over time in the size of the pupil. The second information processor obtains a second moving image including a face and detecting an eye from two or more second images among the second moving
(Continued)

image. The second information processor detects a pupil from the eye detected from the second image, calculating its size, and performing inference on the change over time in the size of the pupil on the basis of the result of the learning performed by the first information processor.

3 Claims, 11 Drawing Sheets

(51) Int. Cl.
  *G06T 7/62* (2017.01)
  *G06V 40/18* (2022.01)
(58) Field of Classification Search
  CPC ............ G06T 2207/30201; G06T 7/73; G06T 2207/10016; G06T 2207/20061; G06T 2207/20076; G06T 2207/20081; G06T 2207/20084; A61B 3/112; A61B 5/1103; A61B 5/168; A61B 5/165
  See application file for complete search history.

(56) References Cited

U.S. PATENT DOCUMENTS

| | | |
|---|---|---|
| 2009/0003709 A1 | 1/2009 | Kaneda et al. |
| 2009/0186470 A1 | 7/2009 | Takahashi et al. |
| 2011/0111558 A1 | 5/2011 | Yamazaki et al. |
| 2014/0091301 A1 | 4/2014 | Yamazaki |
| 2015/0002392 A1* | 1/2015 | Kempinski ............ G06V 40/19 345/156 |
| 2016/0379093 A1* | 12/2016 | Yoshioka ............. G06V 40/166 382/159 |
| 2017/0000344 A1* | 1/2017 | Visconti ............... G06V 40/193 |
| 2017/0095150 A1* | 4/2017 | Sato ......................... A61B 3/02 |
| 2017/0102783 A1 | 4/2017 | Shikii et al. |
| 2017/0205874 A1 | 7/2017 | Miyaguchi |
| 2018/0033362 A1 | 2/2018 | Yamazaki et al. |
| 2018/0075490 A1 | 3/2018 | Chintalapoodi et al. |
| 2019/0073533 A1* | 3/2019 | Chen .................... G06V 40/193 |
| 2019/0099076 A1 | 4/2019 | Fujikado et al. |
| 2019/0159716 A1 | 5/2019 | Alailima et al. |
| 2021/0073096 A1* | 3/2021 | Kato ...................... B25J 9/1676 |
| 2021/0269046 A1* | 9/2021 | Hashimoto .......... G06V 40/174 |
| 2021/0279449 A1 | 9/2021 | Yamazaki et al. |
| 2021/0282639 A1* | 9/2021 | Yokoyama ............... A61B 5/16 |

FOREIGN PATENT DOCUMENTS

| | | | |
|---|---|---|---|
| CN | 105513278 A | | 4/2016 |
| CN | 106137181 A | | 11/2016 |
| JP | 09-218375 A | | 8/1997 |
| JP | 2007-295946 A | | 11/2007 |
| JP | 2012073876 A | * | 4/2012 |
| JP | 2012-212990 A | | 11/2012 |
| JP | 2014-050649 A | | 3/2014 |
| JP | 2015-132783 A | | 7/2015 |
| JP | 2017-169601 A | | 9/2017 |
| KR | 10-1224889 | | 1/2013 |
| KR | 2017-0049997 A | | 5/2017 |
| WO | WO-2012/133021 | | 10/2012 |
| WO | WO-2019/025895 | | 2/2019 |

OTHER PUBLICATIONS

English Machine Translation of CN 102622600 A (Zhang et al., Published Aug. 1, 2012) (Year: 2012).*
International Search Report (Application No. PCT/IB2020/057918) Dated Nov. 17, 2020.
Written Opinion (Application No. PCT/IB2020/057918) Dated Nov. 17, 2020.

* cited by examiner

FIG. 1
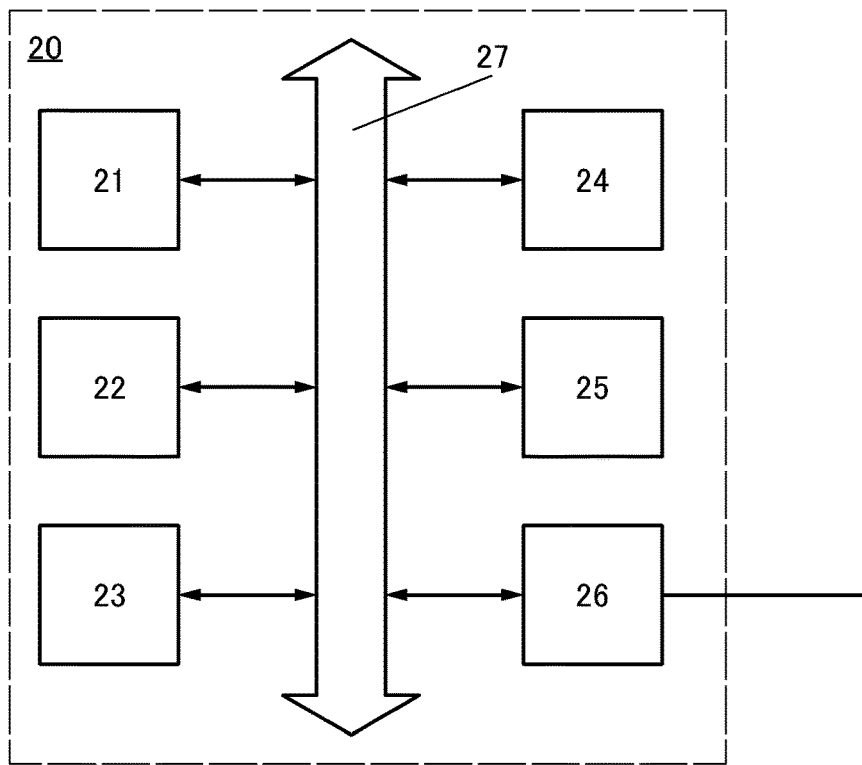
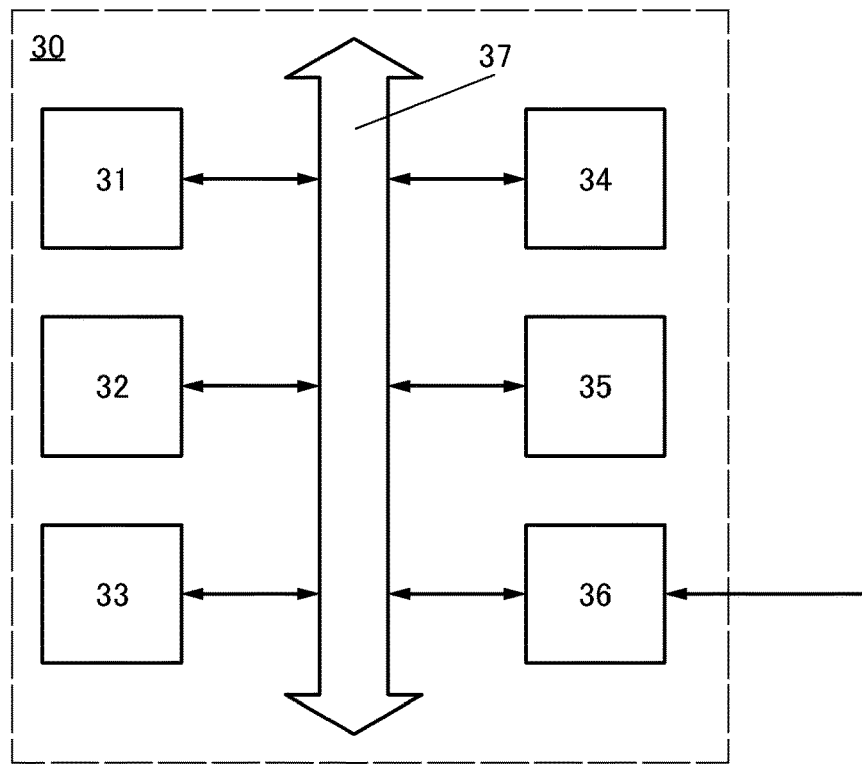

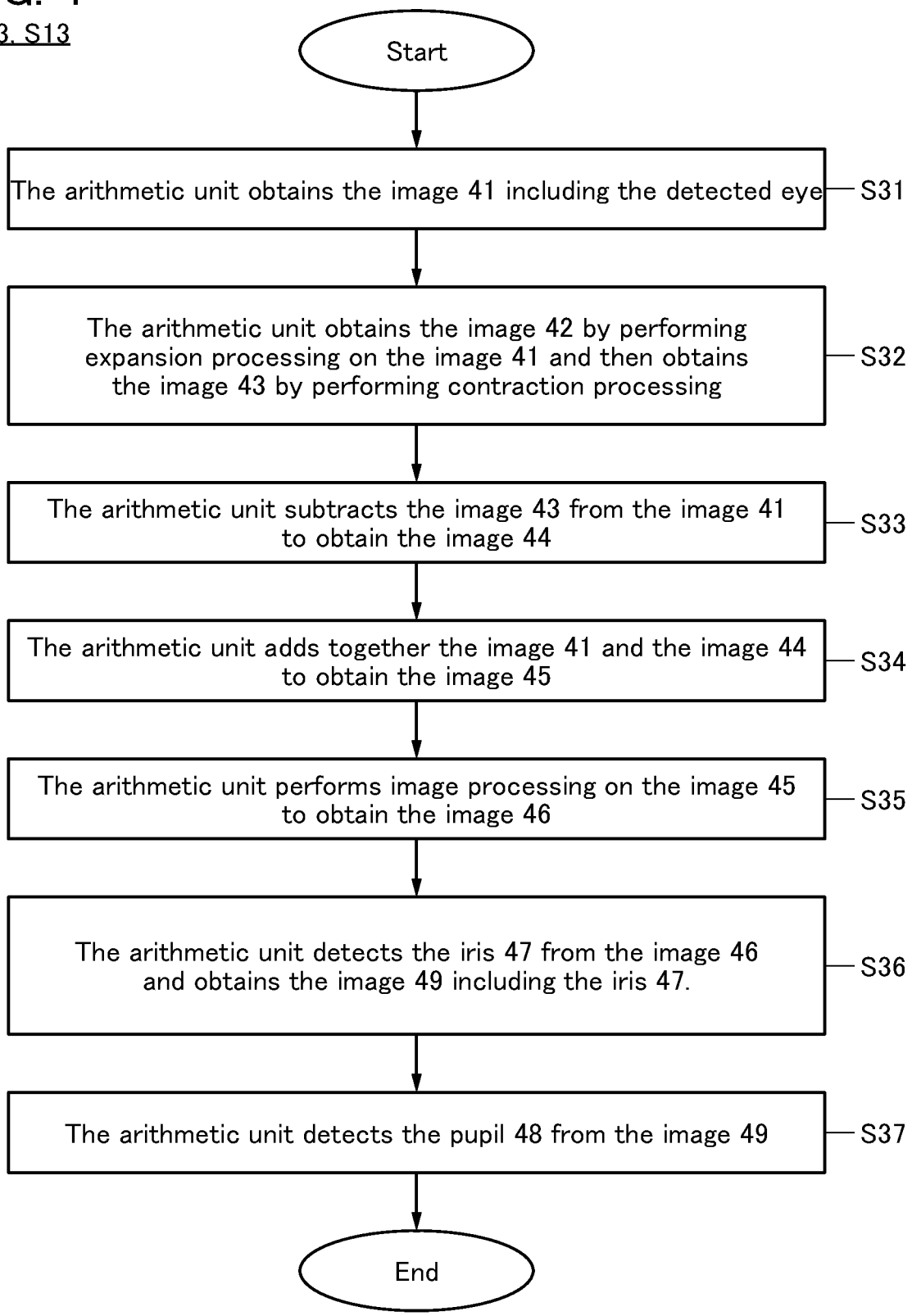

FIG. 7A1
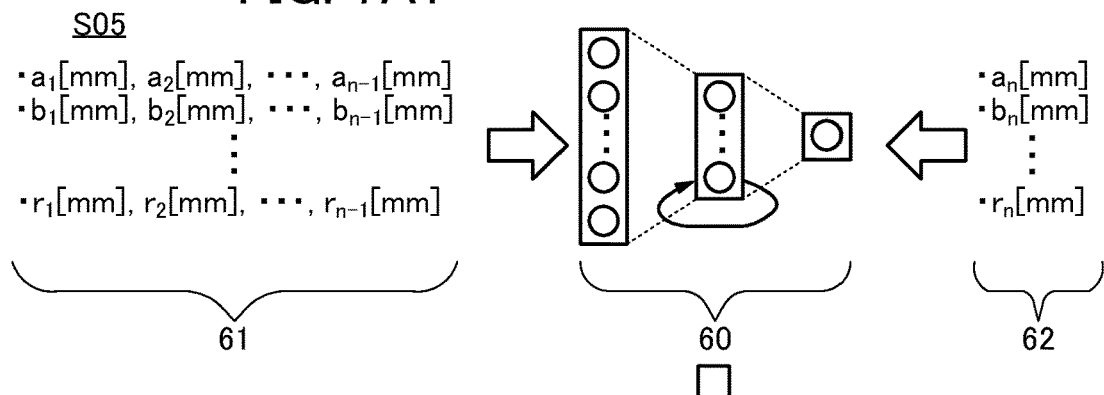
FIG. 7A2
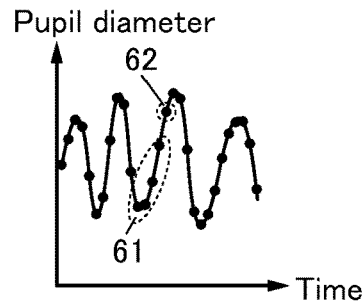
FIG. 7B1
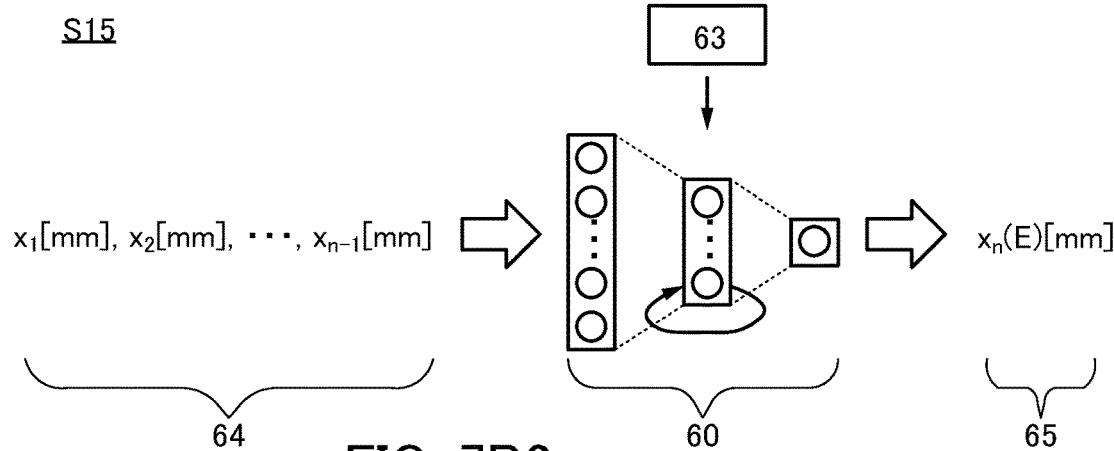
FIG. 7B2
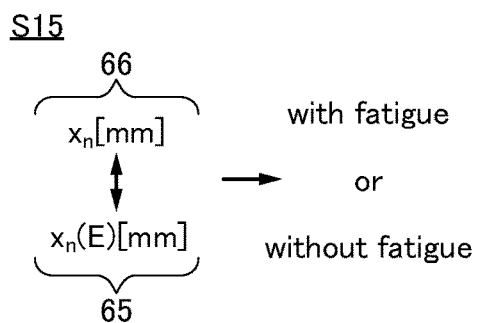

FIG. 10A
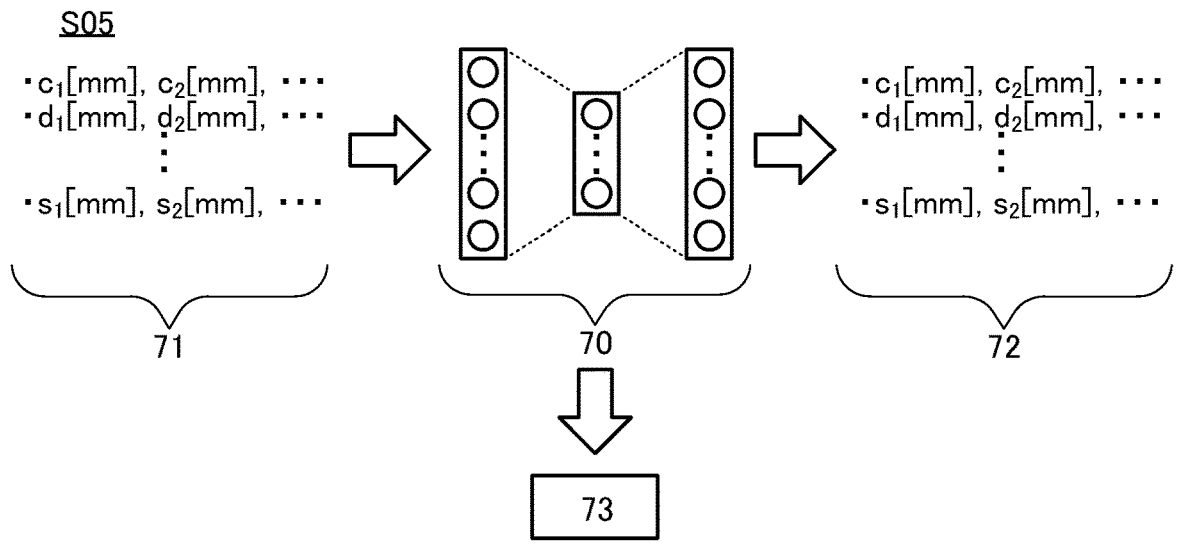
FIG. 10B1
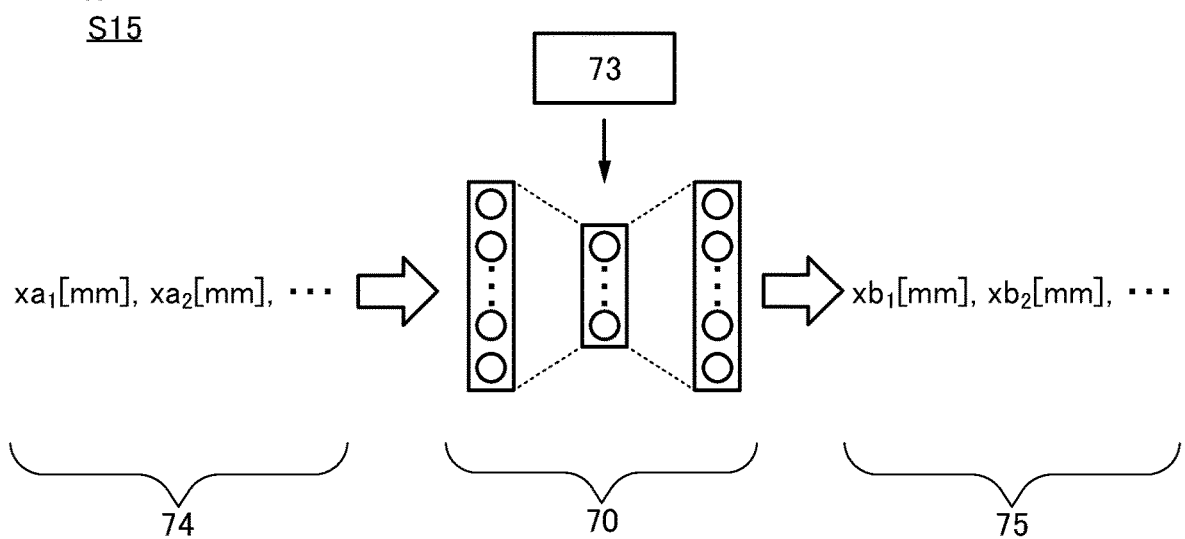
FIG. 10B2
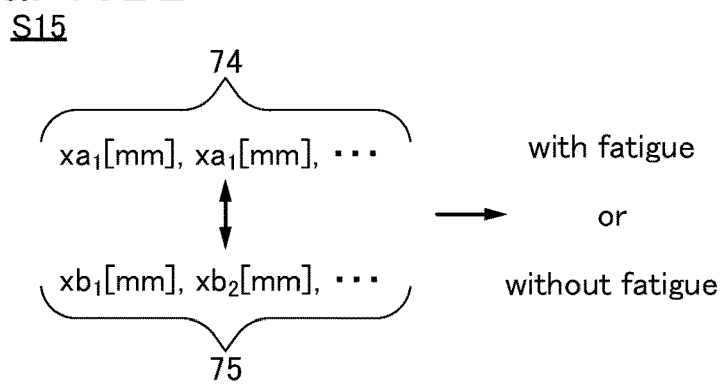

INFORMATION PROCESSOR PERFORMING ARITHMETIC OPERATION USING MACHINE LEARNING

CROSS REFERENCE TO RELATED APPLICATIONS

This application is a U.S. National Phase Application under 35 U.S.C. § 371 of International Application PCT/IB2020/057918, filed on Aug. 25, 2020, which is incorporated by reference and claims the benefit of a foreign priority application filed in Japan on Sep. 6, 2019, as Application No. 2019-162687.

TECHNICAL FIELD

One embodiment of the present invention relates to an information processor. Another embodiment of the present invention relates to an information processing system. Another embodiment of the present invention relates to an information processing method. Another embodiment of the present invention relates to an information terminal.

BACKGROUND ART

A user may feel fatigue, drowsiness, or the like when the user uses an information terminal such as a smartphone or a tablet for a long time. In particular, the user may feel eye fatigue by gazing at a screen of the information terminal for a long time. Patent Document 1 discloses a detection device and a detection method for eye fatigue.

A pupil diameter changes depending on whether there is fatigue, drowsiness, or the like. For example, when there is fatigue or drowsiness, the pupil diameter becomes smaller than that in the case where there is no fatigue or drowsiness. The pupil diameter generally changes periodically; however, in the case where there is fatigue or drowsiness, the change cycle of the pupil diameter becomes longer than that in the case where there is no fatigue or drowsiness.

REFERENCE

Patent Document

[Patent Document 1] Japanese Published Patent Application No. 2017-169601

SUMMARY OF THE INVENTION

Problems to be Solved by the Invention

It is preferable that fatigue, drowsiness, or the like of the user be able to be detected in real time during the use of the information terminal such as the smartphone or the tablet, in which case, for example, the operation of the information terminal can be changed according to whether the user has fatigue, drowsiness or the like. In the case where fatigue, drowsiness, or the like of the user is detected in real time, the information terminal in use itself preferably has a function of presuming the fatigue, drowsiness, or the like of the user. However, in order to detect eye fatigue by the method disclosed in Patent Document 1, a dedicated device is necessary.

An object of one embodiment of the present invention is to provide an information processor having a function of detecting fatigue, drowsiness, or the like of the user in real time. Another object of one embodiment of the present invention is to provide an information processor having a function of presuming fatigue, drowsiness, or the like of the user with high accuracy. Another object of one embodiment of the present invention is to provide an information processor having a function of presuming fatigue, drowsiness, or the like of the user by a simple method. Another object of one embodiment of the present invention is to provide an information processor having a function of presuming fatigue, drowsiness, or the like of the user in a short time.

An object of one embodiment of the present invention is to provide an information processing system having a function of detecting fatigue, drowsiness, or the like of the user in real time. Another object of one embodiment of the present invention is to provide an information processing system having a function of presuming fatigue, drowsiness, or the like of the user with high accuracy. Another object of one embodiment of the present invention is to provide an information processing system having a function of presuming fatigue, drowsiness, or the like of the user by a simple method. Another object of one embodiment of the present invention is to provide an information processing system having a function of presuming fatigue, drowsiness, or the like of the user in a short time.

Note that the description of a plurality of objects does not preclude the existence of each object. One embodiment of the present invention does not necessarily achieve all the objects described as examples. Furthermore, objects other than those listed are apparent from description of this specification, and such objects can be objects of one embodiment of the present invention.

Means for Solving the Problems

One embodiment of the present invention is an information processor including an imaging unit and an arithmetic unit having a function performing arithmetic operation by machine learning, in which the imaging unit has a function of obtaining a moving image that is a group of images of two or more frames, the arithmetic unit has a function of detecting a first object from each of two or more of the images included in the moving image, the arithmetic unit has a function of detecting a second object from each of the detected first objects, the arithmetic unit has a function of calculating a size of each of the detected second objects, and the arithmetic unit has a function of performing machine learning using a change over time in the size of the second object.

In the above embodiment, the machine learning may be performed with a neural network.

In the above embodiment, the moving image may include a face, the first object may be an eye, and the second object may be a pupil.

One embodiment of the present invention is an information processor having a function of performing inference on the basis of a learning result obtained by performing learning using a change over time in a size of a first object shown in two or more first images included in a first moving image. The information processor has a function of obtaining a second moving image, the information processor has a function of detecting a second object from each of two or more second images included in the second moving image, the information processor has a function of detecting a third object from each of the detected second objects, the information processor has a function of calculating a size of each of the detected third objects, and information processor has a function of performing inference on a change over time in the size of the third object on the basis of the learning result.

In the above embodiment, the learning and the inference may be performed with a neural network, and the learning result may include a weighting coefficient.

In the above embodiment, the first moving image may include a first face, the second moving image may include a second face, the first and third objects may be pupils, and the second object may be an eye.

In the above embodiment, the information processor may have a function of presuming fatigue of a person including the second face.

Effect of the Invention

According to one embodiment of the present invention, an information processor having a function of detecting fatigue, drowsiness, or the like of the user in real time can be provided. According to another embodiment of the present invention, an information processor having a function of presuming fatigue, drowsiness, or the like of the user with high accuracy can be provided. According to another embodiment of the present invention, an information processor having a function of presuming fatigue, drowsiness, or the like of the user by a simple method can be provided. According to another embodiment of the present invention, an information processor having a function of presuming fatigue, drowsiness, or the like of the user in a short time can be provided.

According to one embodiment of the present invention, an information processing system having a function of detecting fatigue, drowsiness, or the like of the user in real time can be provided. According to another embodiment of the present invention, an information processing system having a function of presuming fatigue, drowsiness, or the like of the user with high accuracy can be provided. According to another embodiment of the present invention, an information processing system having a function of presuming fatigue, drowsiness, or the like of the user by a simple method can be provided. According to another embodiment of the present invention, an information processing system having a function of presuming fatigue, drowsiness, or the like of the user in a short time can be provided.

Note that description of the plurality of effects does not preclude the existence of other effects. One embodiment of the present invention does not necessarily achieve all the effects described as examples. In one embodiment of the present invention, other objects, effects, and novel features will be apparent from the description of the specification and the drawings.

BRIEF DESCRIPTION OF THE DRAWINGS

FIG. 1 is a block diagram illustrating a structure example of an information processing system.

FIG. 4 is a flow chart showing an example of a method for operating the information processor.

FIG. 7A1, FIG. 7A2, FIG. 7B1, and FIG. 7B2 are schematic views illustrating examples of a method for operating the information processor.

FIG. 10A, FIG. 10B1, and FIG. 10B2 are schematic views illustrating an example of a method for operating the information processor.

MODE FOR CARRYING OUT THE INVENTION

Figure 2:
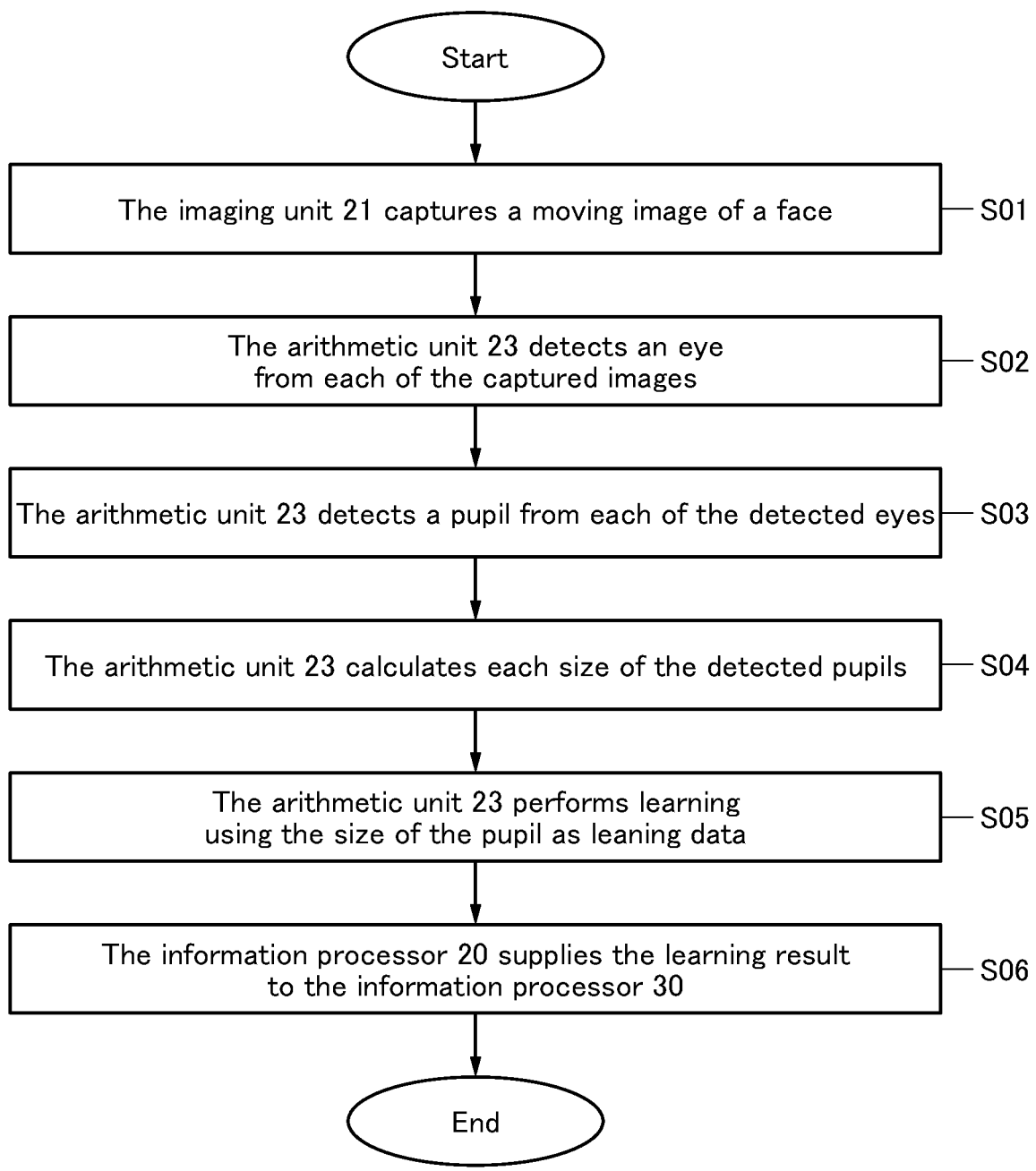
FIG. 2 is a flow chart showing an example of a method for operating an information processor.

Embodiments of the present invention will be described below. Note that one embodiment of the present invention is not limited to the following description, and it will be readily appreciated by those skilled in the art that modes and details of the present invention can be modified in various ways without departing from the spirit and scope of the present invention. One embodiment of the present invention therefore should not be construed as being limited to the following description of the embodiments.

Note that in the drawings attached to this specification, the block diagram in which components are classified according to their functions and shown as independent blocks is illustrated; however, it is difficult to separate actual components completely according to their functions, and one component may be related to a plurality of functions or a plurality of components may achieve one function.

Embodiment 1

In this embodiment, an information processing system of one embodiment of the present invention and an information processing method using the information processing system will be described. With the information processing system of one embodiment of the present invention and the information processing method, fatigue, drowsiness, or the like of a user of an information terminal such as a smartphone or a tablet can be presumed. In particular, eye fatigue of the user of the information terminal can be detected.

<Structure Example of Information Processing System>

FIG. 1 is a block diagram illustrating a structure example of an information processing system 10 that is the information processing system of one embodiment of the present invention. The information processing system 10 includes an information processor 20 and an information processor 30.

The information processor 20 includes an imaging unit 21, a display unit 22, an arithmetic unit 23, a main memory unit 24, an auxiliary memory unit 25, and a communication unit 26. Data or the like can be transmitted between components included in the information processor 20 via a transmission path 27. The information processor 30 includes an imaging unit 31, a display unit 32, an arithmetic unit 33, a main memory unit 34, an auxiliary memory unit 35, and a communication unit 36. Data or the like can be transmitted between components included in the information processor 30 via a transmission path 37.

The imaging unit 21 and the imaging unit 31 have a function of performing image capturing and obtaining imaging data. The display unit 22 and the display unit 32 have a function of displaying an image.

The arithmetic unit 23 and the arithmetic unit 33 have a function of performing arithmetic processing. The arithmetic unit 23 has a function of performing predetermined arithmetic processing, for example, on data transmitted from the imaging unit 21, the main memory unit 24, the auxiliary memory unit 25, or the communication unit 26 to the arithmetic unit 23 via the transmission path 27. The arithmetic unit 33 has a function of performing predetermined arithmetic processing, for example, on data transmitted from the imaging unit 31, the main memory unit 34, the auxiliary memory unit 35, or the communication unit 36 to the arithmetic unit 33 via the transmission path 37. The arithmetic unit 23 and the arithmetic unit 33 have a function of performing arithmetic operation by machine learning. The arithmetic unit 23 and the arithmetic unit 33 have a function of performing arithmetic operation using a neural network, for example. The arithmetic unit 23 and the arithmetic unit 33 can include a CPU (Central Processing Unit) and a GPU (Graphics Processing Unit), for example.

The main memory unit 24 and the main memory unit 34 have a function of storing data, a program, and the like. The arithmetic unit 23 can execute arithmetic processing by reading the data, the program, and the like stored in the main memory unit 24. The arithmetic unit 23, for example, can execute predetermined arithmetic processing on the data read from the main memory unit 24 by executing the program read from the main memory unit 24. The arithmetic unit 33 can execute arithmetic processing by reading the data, the program, and the like stored in the main memory unit 34. The arithmetic unit 33, for example, can execute predetermined arithmetic processing on the data read from the main memory unit 34 by executing the program read from the main memory unit 34.

The main memory unit 24 and the main memory unit 34 preferably operate at higher speed than the auxiliary memory unit 25 and the auxiliary memory unit 35. For example, the main memory unit 24 and the main memory unit 34 can include a DRAM (Dynamic Random Access Memory), an SRAM (Static Random Access Memory), or the like.

The auxiliary memory unit 25 and the auxiliary memory unit 35 have a function of storing data, a program, and the like for a longer period than the main memory unit 24 and the main memory unit 34. The auxiliary memory unit 25 and the auxiliary memory unit 35 can include an HDD (Hard Disk Drive), an SSD (Solid State Drive), or the like, for example. Furthermore, the auxiliary memory unit 25 and the auxiliary memory unit 35 may include a nonvolatile memory such as an ReRAM (Resistive Random Access Memory, also referred to as a resistance-change memory), a PRAM (Phase change Random Access Memory), an FeRAM (Ferroelectric Random Access Memory), an MRAM (Magnetoresistive Random Access Memory, also referred to as a magnetoresistive memory), or a flash memory.

The communication unit 26 has a function of transmitting and receiving data or the like to/from a device or the like provided outside the information processor 20. The communication unit 36 has a function of transmitting and receiving data or the like to/from a device or the like provided outside the information processor 30. For example, it is possible to supply data or the like from the information processor 20 to the information processor 30 by supplying data or the like from the communication unit 26 to the communication unit 36. Furthermore, the communication unit 26 and the communication unit 36 can have a function of supplying data or the like to a network and a function of obtaining data or the like from the network.

Here, in the case where the arithmetic unit 23 and the arithmetic unit 33 have a function of performing arithmetic operation by machine learning, for example, the arithmetic unit 23 can perform learning and the learning result can be supplied from the information processor 20 to the information processor 30. For example, in the case where the arithmetic unit 23 and the arithmetic unit 33 have a function of performing arithmetic operation using a neural network, the arithmetic unit 23 can obtain a weighting coefficient or the like by performing learning, and the weighting coefficient or the like can be supplied from the information processor 20 to the information processor 30. In the above manner, even when the arithmetic unit 33 provided in the information processor 30 does not perform learning, inference on data that has been input to the arithmetic unit 33 can be performed on the basis of a learning result by the arithmetic unit 23 provided in the information processor 20. Accordingly, the arithmetic throughput of the arithmetic unit 33 can be lower than that of the arithmetic unit 23.

In the case where the arithmetic unit 23 performs learning and the learning result is supplied from the information processor 20 to the information processor 30, the information processor 20 can be provided in a server, for example. Note that in the case where the information processor 20 is provided in the server, the imaging unit 21 and the display unit 22 are not necessarily provided in the information processor 20. That is, the imaging unit 21 and the display unit 22 may be provided outside the information processor 20.

The information processor 30 can be provided in an information terminal such as a smartphone, a tablet, or a personal computer, for example. At least a part of the components of the information processor 20 and at least a part of the components of the information processor 30 may be both provided in the server. For example, the arithmetic unit 23 and the arithmetic unit 33 may be provided in the server. In this case, for example, data obtained by the information terminal is supplied to the arithmetic unit 33 via a network and the arithmetic unit 33 provided in the server performs inference or the like on the data. Then, the inference result is supplied to the information terminal via the network, whereby the information terminal can obtain the inference result.

<Example of Information Processing Method>

An example of an information processing method using the information processing system 10 will be described below. Specifically, an example of a method for presuming fatigue, drowsiness, or the like of the user of the information terminal provided with the information processor 30 included in the information processing system 10 by arithmetic operation using machine learning will be described.

Figure 3:
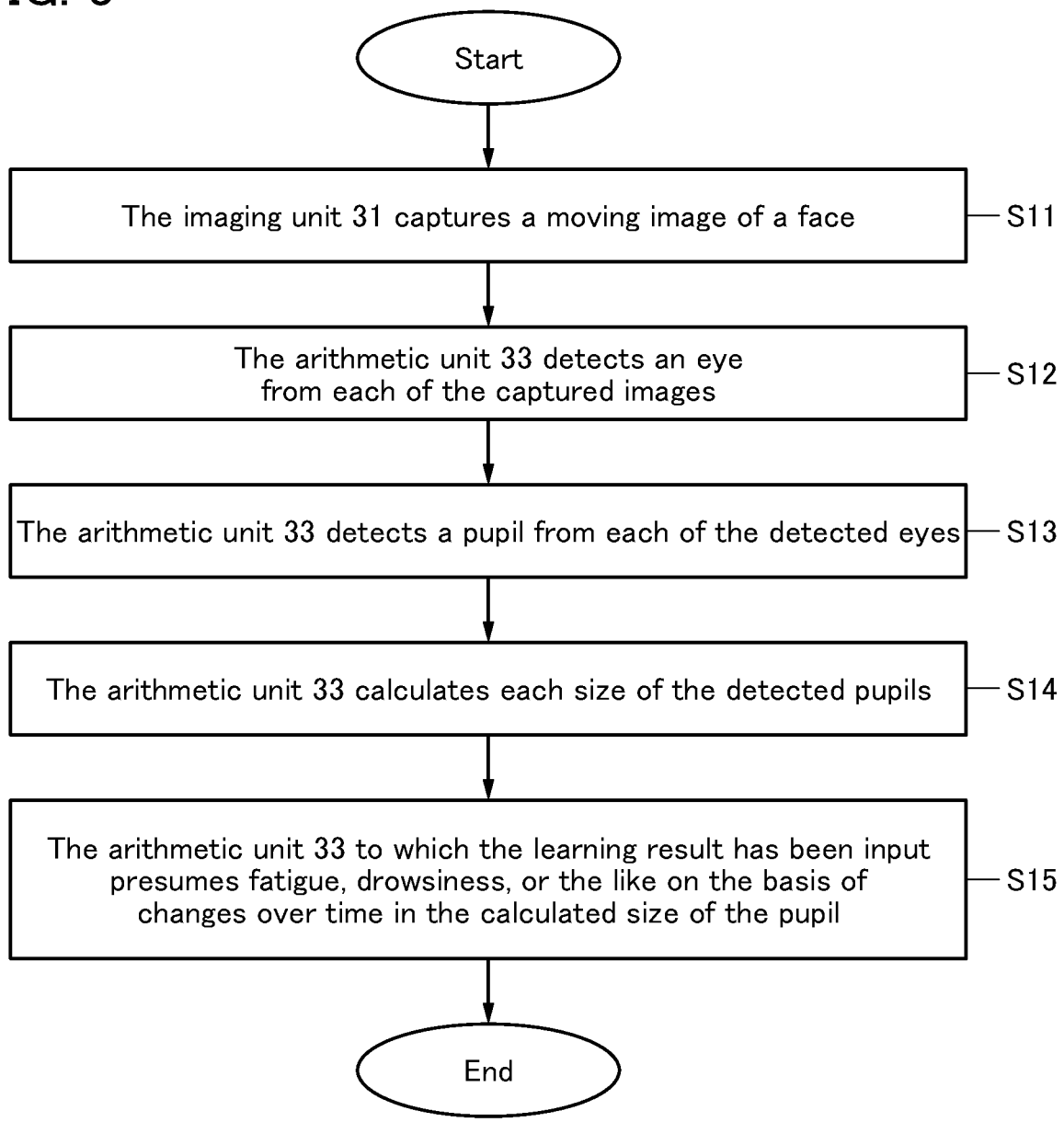
FIG. 3 is a flow chart showing an example of a method for operating an information processor.

FIG. 2 and FIG. 3 are flow charts showing an example of a method for presuming fatigue, drowsiness, or the like by arithmetic operation using machine learning. Learning is shown in FIG. 2 and inference is shown in FIG. 3.

An example of a learning method will be described with reference to FIG. 2 and the like. First, the imaging unit 21 captures a moving image. For example, the imaging unit 21 captures a moving image including a human face (Step S01). Here, the moving image refers to a group of images of two or more frames. Although details will be described later, learning data is produced on the basis of the moving image captured by the imaging unit 21 and the arithmetic unit 23 performs learning. Thus, for example, in the case where the imaging unit 21 captures a moving image including a human face, it is preferable that the imaging unit 21 capture a moving image for a large number of people that differ in sex, race, physical constitution, and the like.

Note that image processing may be performed on the moving image captured by the imaging unit 21. For example, noise removal, gray-scale transformation, normalization, contrast adjustment, and the like can be performed. Furthermore, binarization or the like may be performed on the images included in the moving image. By such processing, a later step can be performed with high accuracy. For example, detection of a first object performed in Step S02, which will be described later, can be performed with high accuracy.

Next, the arithmetic unit 23 detects a first object from each of the captured images. For example, in the case where a moving image of a human face is captured in Step S01, the first object can be an eye (Step S02). The first object, for example, can be detected with a cascade classifier. The detection can be performed with, for example, Haar Cascades. Note that in the case where the first object is an eye and both eyes are included in one image, only one of the eyes can be detected.

After that, the arithmetic unit 23 detects a second object from each of the detected first objects. For example, when the first object is an eye, the second object can be a pupil (Step S03). The pupil can be detected from the eye by circular extraction, for example. Details of the method for detecting the pupil from the eye will be described later.

Here, the pupil is a hole surrounded by an iris and can be referred to as a "black part of the eye." The pupil has a function of adjusting the amount of light entering a retina. The iris is a thin film positioned between a cornea and a lens and can be regarded as a colored portion in the eye, for example.

Next, the arithmetic unit 23 calculates each size of the detected second objects (Step S04). For example, in the case where the second object is detected by circular extraction, the radius or diameter of the second object can be regarded as the size of the second object. In the case where the shape of the second object is extracted as an elliptical shape, the length of the major axis and the length of the minor axis can be regarded as the size of the second object. The area of the second object can be regarded as the size of the second object.

Then, the arithmetic unit 23 performs learning using the size of the second object to obtain the learning result (Step S05). Specifically, the learning result is obtained on the basis of a change over time in the size of the second object. The learning can be performed using a neural network, for example. In this case, the learning result can be a weighting coefficient or the like as described above. Details of the learning method will be described later.

Next, the information processor 20 supplies the learning result to the information processor 30 (Step S06). Specifically, the learning result obtained by the arithmetic unit 23 is transmitted to the communication unit 26 via the transmission path 27 and then supplied from the communication unit 26 to the communication unit 36. The learning result supplied to the communication unit 36 can be stored in the auxiliary memory unit 35. In addition, the learning result may be stored in the auxiliary memory unit 25.

Next, an example of an inference method on the basis of the learning result obtained by the method shown in the FIG. 2 or the like will be described with reference to FIG. 3 and the like. First, the imaging unit 31 captures a moving image. For example, the imaging unit 31 captures a moving image including the face of the user of the information terminal provided with the information processor 30 (Step S11). Note that in the case where image processing is performed on the moving image captured by the imaging unit 21 in Step S01 shown in FIG. 2, similar image processing is preferably performed on the moving image captured by the imaging unit 31, in which case inference can be performed with high accuracy.

Next, the arithmetic unit 33 detects a first object from each of images included in the captured moving image. For example, in the case where a moving image of a human face is captured in Step S11, the first object can be an eye (Step S12). The first object can be detected by a method similar to the detection method used in Step S02 shown in FIG. 2.

After that, the arithmetic unit 33 detects a second object from each of the detected first objects. For example, when the first object is an eye, the second object can be a pupil (Step S13). The second object can be detected by a method similar to the detection method used in Step S03 shown in FIG. 2.

Next, the arithmetic unit 33 calculates each size of the detected second objects (Step S14). A method similar to that used in Step S04 shown in FIG. 2 can be used as the method for calculating the size.

Then, the arithmetic unit 33 to which the learning result obtained by the arithmetic unit 23 in Step S05 shown in FIG. 2 has been input performs inference on the basis of a change over time in the size of the second object. For example, in the case where the face of the user of the information terminal provided with the information processor 30 is included in the moving image captured by the imaging unit 31 and the second object is the pupil of the eye of the user, the arithmetic unit 33 can presume fatigue, drowsiness, or the like of the user (Step S15). Details of the inference method will be described later.

Note that the size of the pupil changes depending on not only whether there is fatigue, drowsiness, or the like, but also, for example, the brightness of the environment. Therefore, for example, a plurality of moving images are preferably captured for the face of the same person under various brightness of the environment in Step S01 shown in FIG. 2. Thus, fatigue, drowsiness, or the like of the user of the information terminal provided with the information processor 30 can be presumed with high accuracy regardless of, for example, the brightness of the environment.

In one embodiment of the present invention, the information processor 30 having a function of presuming fatigue, drowsiness, or the like as described above is provided in an information terminal such as a smartphone, a tablet, or a personal computer. This makes it possible to detect fatigue, drowsiness, or the like of the user of the information terminal in real time without using a dedicated device.

[Example of Method for Detecting Pupil]

Next, an example of the method for detecting a pupil performed in Step S03 and Step S13 will be described. FIG. 4 is a flow chart showing an example of the method for detecting a pupil.

Figure 5A:
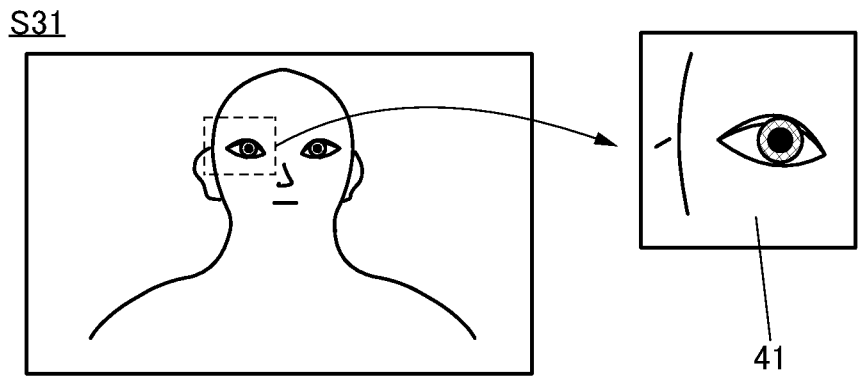
FIG. 5A, FIG. 5B, and FIG. 5C are schematic views illustrating an example of a method for operating the information processor.

First, the arithmetic unit obtains an image 41 that is an image including the detected eye (Step S31). FIG. 5A is a schematic view illustrating Step S31. As illustrated in FIG. 5A, the arithmetic unit obtains the image 41 including the eye detected from the image captured by the imaging unit. Specifically, in Step S03, the arithmetic unit 23 obtains, as the image 41, the image including the eye detected in Step S02 by the arithmetic unit 23. Furthermore, in Step S13, the arithmetic unit 33 obtains, as the image 41, the image including the eye detected in Step S12 by the arithmetic unit 33. Note that when the image captured by the imaging unit is a color image, the arithmetic unit may convert the image 41 into a gray-scale image after the arithmetic unit obtain the image 41.

Figure 5B:
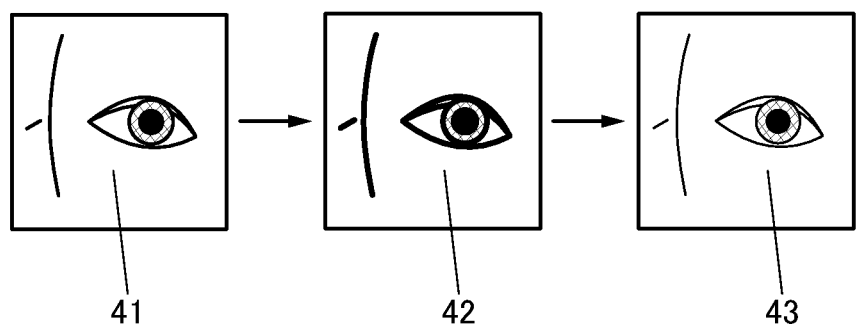

Next, the arithmetic unit obtains an image 42 by performing expansion processing on the image 41, and then performs contraction processing to obtain an image 43 (Step S32). That is, closing processing is performed on the image 41, whereby the image 43 is obtained. FIG. 5B is a schematic view illustrating the expansion processing and the contraction processing.

After that, the arithmetic unit subtracts the image 43 from the image 41 to obtain an image 44 (Step S33). That is, the image 44 is an image expressed by a difference between the image 41 and the image 43. In Step S33, the arithmetic unit can obtain the image 44 by performing Black-hat conversion using the image 41 and the image 43.

Next, the arithmetic unit adds together the image 41 obtained in Step S31 and the image 44 obtained in Step S33 to obtain an image 45 (Step S34). Note that in the case where the image 41 is converted into a gray-scale image in Step S31, the image 41 after gray-scale transformation and the image 44 can be added together in Step S34.

Note that all or part of the processing shown in Step S32 to Step S34 is not necessarily performed. Alternatively, processing other than the processing shown in Step S32 to Step S34 may be performed.

Then, the arithmetic unit performs image processing on the image 45 to obtain an image 46 (Step S35). For example, the arithmetic unit performs processing such as noise removal and smoothing on the image 45. Furthermore, processing such as edge detection and binarization is performed. Specifically, for example, noise removal by a median value filter and smoothing by a Gaussian filter are performed on the image 45, and then edge detection by a Canny method and binarization processing are performed. Note that the noise removal may be performed by a moving average filter, for example. The smoothing may be performed by a moving average filter or a median filter, for example. Furthermore, the edge detection may be performed by a Laplacian filter.

Next, the arithmetic unit detects an iris 47 from the image 46. The iris 47 can be detected using Hough transform, for example. In the case of using Hough transform, the iris 47 can be detected as a circular shape, for example. Alternatively, the iris 47 can be detected as an elliptical shape, for example. Note that the iris 47 may be detected using generalized Hough transform.

Then, the arithmetic unit obtains an image 49 including the detected iris 47 (Step S36). For example, the image 49 is extracted from the image 46 on the basis of the coordinates of the detected iris 47 in the image 46.

Figure 5C:
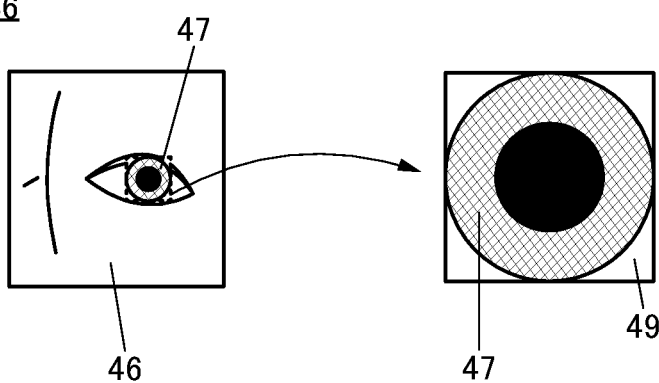

FIG. 5C is a schematic view illustrating Step S36. For example, the image 49 can be a rectangle whose four sides are in contact with the iris 47 as illustrated in FIG. 5C. For example, in the case where the iris 47 is detected as a circular shape, the image 49 can be a square whose four sides are in contact with the iris 47. Note that each side of the image 49 is not necessarily in contact with the iris 47. For example, an image with a predetermined number of pixels, in which the iris 47 is positioned in the center, may be the image 49.

Next, the arithmetic unit detects a pupil 48 from the image 49 (Step S37). The pupil 48 is detected from the image 49 by arithmetic operation using a neural network, for example.

Step S37 is performed using a generator on which learning has been performed in advance. Here, the generator is a program performing arithmetic operation by machine learning and has a function of outputting data corresponding to input data. Specifically, learning enables the generator to make an inference on the data input to the generator.

Figure 6A:
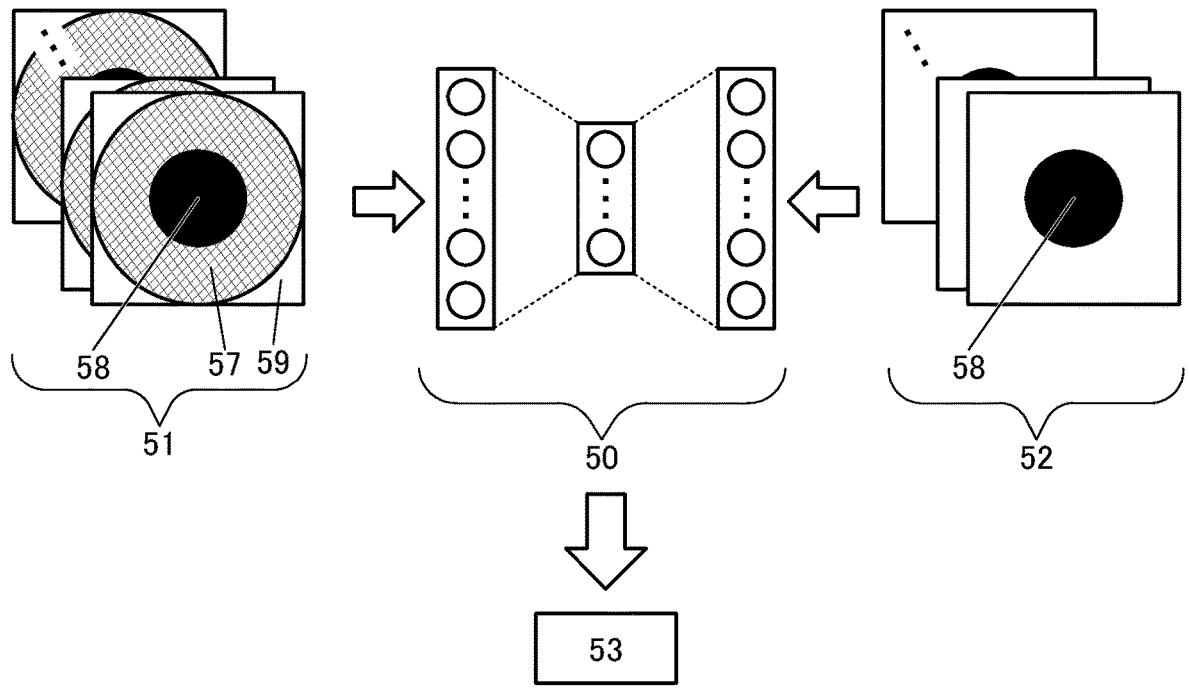
FIG. 6A and FIG. 6B are schematic views illustrating examples of a method for operating the information processor.

FIG. 6A is a schematic view illustrating the above-described learning. Here, a generator that performs learning is referred to as a generator 50. In the case where a neural network is used as the generator 50, a convolutional neural network (CNN) can be used as the generator 50. In particular, U-net as one kind of CNN is preferably used. In U-net, an input image is subjected to down-sampling by convolution, and then subjected to up-sampling by deconvolution using a feature value obtained by the down-sampling. The arithmetic unit 23 and the arithmetic unit 33 can have a function of the generator 50.

Learning of the generator 50 can be performed by supervised learning using data 51 and data 52. The data 51 can be a group of images 59. The image 59 includes an iris 57 and a pupil 58. The image 59 can be obtained by the information processor 20 by a method similar to Step S01 and Step S02 shown in FIG. 2 and Step S31 to Step S36 shown in FIG. 4. Note that the imaging unit 21 captures the moving image of the face in Step S01; in the case where the image 59 is obtained, however, the imaging unit 21 does not necessarily capture the moving image. For example, the imaging unit 21 may capture one (one-frame) image for each person.

The data 52 is data indicating the coordinates of the pupil 58 included in the image 59. Specifically, the data 52 can be a binary image in which the pupil 58 portion has a different color from the other portion. The data 52 can be obtained, for example, by filling the pupil 58 included in the image 59. Alternatively, the data 52 can be obtained in such a manner that an image including an eye is obtained by a method similar to Step S31 shown in FIG. 4, and then the pupil 58 included in the image including the eye is filled.

The learning of the generator 50 is performed so that output data can become closer to the data 52 when the data 51 is input to the generator 50. That is, the learning of the generator 50 is performed using the data 52 as correct data. By the learning of the generator 50, the generator 50 generates a learning result 53. In the case where a neural network is used as the generator 50, the learning result 53 can be a weighting coefficient or the like.

The learning of the generator 50, that is, the generation of the learning result 53 can be performed by, for example, the arithmetic unit 23 included in the information processor 20. Then, when the learning result 53 is supplied from the information processor 20 to the information processor 30, the arithmetic unit 33 can also perform inference similar to that of the arithmetic unit 23. The learning result 53 generated by the arithmetic unit 23 can be stored in the auxiliary memory unit 25, for example. In addition, the learning result 53 generated by the arithmetic unit 23 and supplied to the information processor 30 can be stored in the auxiliary memory unit 35, for example.

Through the above steps, the learning of the generator 50 is terminated.

Figure 6B:
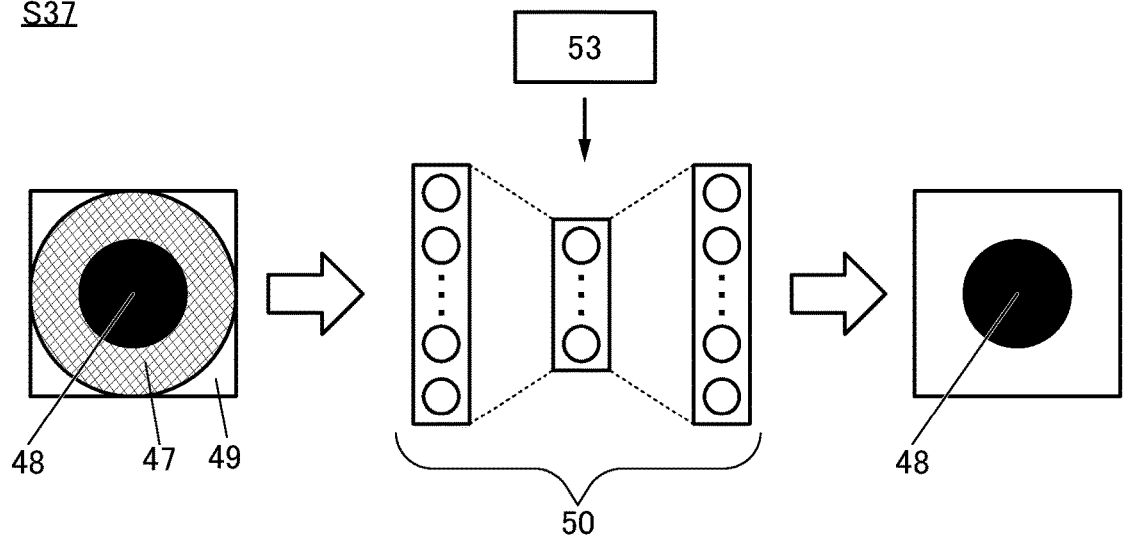

FIG. 6B is a schematic view illustrating Step S37. That is, FIG. 6B is a schematic view illustrating detection of the pupil 48 from the image 49.

As illustrated in FIG. 6B, in Step S37, the image 49 obtained by the arithmetic unit in Step S36 is input to the generator 50 in which the learning result 53 has been read. Thus, the generator 50 can perform inference on the image 49 and output data indicating the coordinates of the pupil 48. For example, the generator 50 can output a binary image in which the color of the pupil 48 is made different from the color of the other portion.

By the above-described method, in Step S03 or Step S13, the pupil can be detected from the eye detected in Step S02 or Step S12.

Detection of a pupil by arithmetic operation using machine learning can be performed in a shorter time than that in the case where, for example, a pupil is visually detected. Furthermore, for example, even when the pupil reflects a surrounding landscape, the pupil can be detected with high accuracy.

Note that the method for detecting the pupil 48 in Step S37 is not limited to the method illustrated in FIG. 6A and FIG. 6B. For example, the image 49 may be a color image, and after the color image 49 is subjected to gray-scale transformation, edge detection of the pupil 48 may be performed. Then, after the edge detection, the pupil 48 may be detected.

The gray-scale transformation of the image 49 can be performed using partial least squares (PLS) regression, for example. By the gray-scale transformation of the image 49, a difference between the brightness of the pupil 48 and the brightness of the iris 47 can be large. Accordingly, the boundary between the pupil 48 and the iris 47 can be emphasized; thus, the edge detection of the pupil 48 can be performed with high accuracy. Therefore, the pupil 48 can be detected with high accuracy.

The edge detection of the pupil 48 can be performed by, for example, a Canny method or a Laplacian filter. Furthermore, detection of the pupil 48 after the edge detection can be performed using Hough transform, for example. In the case of using Hough transform, the pupil 48 can be detected as a circular shape, for example. Alternatively, the pupil 48 can be detected as an elliptical shape, for example. Note that the pupil 48 may be detected using generalized Hough transform.

In the case where not only the iris but also the pupil is detected in Step S03 or Step S13, image capturing can be performed using infrared rays in Step S01 or Step S11. An iris reflects infrared rays. In contrast, a pupil does not reflect infrared rays. Therefore, the iris and the pupil can be clearly distinguished from each other by image capturing using infrared rays in Step S01 or Step S11. Thus, the pupil can be detected with high accuracy.

[Example_1 of Method for Presuming Fatigue, Drowsiness, or the Like]

Next, an example of a method for presuming fatigue, drowsiness, or the like of the user of the information terminal provided with the information processor 30 by arithmetic operation using machine learning will be described. Specifically, an example of the learning method using the size of a pupil, which is performed in Step S05, will be described. In addition, an example of the method for presuming fatigue, drowsiness, or the like by inference based on the learning result, which is performed in Step S15, will be described. Note that the following description is made on the assumption that the second object is a pupil.

FIG. 7A1 is a schematic view illustrating Step S05. In Step S05, learning of a generator 60 that is a program performing arithmetic operation by machine learning is performed. A neural network can be used as the generator 60. Time series data such as a change over time in the size of a pupil is input to the generator 60, the details of which will be described later. Thus, in the case where a neural network is used as the generator 60, a recurrent neural network (RNN) is preferably used as the generator 60. Alternatively, a long short-term memory (LSTM) is preferably used as the generator 60. Alternatively, a gated recurrent unit (GRU) is preferably used.

The learning of the generator 60 can be performed using data 61 and data 62. The data 61 is the data obtained in Step S04 and can be a change over time in the size of the pupil. As described above, for example, in the case where the pupil is detected by circular extraction, the radius or diameter of the pupil can be regarded as the size of the pupil. In addition, in the case where the pupil is extracted as an elliptical shape, the length of the major axis and the length of the minor axis can be regarded as the size of the pupil. Moreover, the area of the pupil can be regarded as the size of the pupil. In FIG. 7A1, a change over time in the size of the pupil from Time 1 to n−1 (n is an integer greater than or equal to 3) is regarded as the data 61.

The data 61 may be a change over time in the ratio between the size of the pupil and the size of the iris. In this case, it is preferable that the iris and the pupil be extracted as the same kind of shapes. For example, when the iris is extracted as a circular shape, the pupil is also extracted as a circular shape. When the iris is extracted as an elliptical shape, the pupil is also extracted as an elliptical shape. When the data 61 is the change over time in the ratio between the size of the pupil and the size of the iris is detected, for example, by the method shown in Step S37, the resolutions of the images 49 including the iris 47 and the pupil 48 can differ from each other. For example, the resolution of the image 49 including the iris 47 and the pupil 48 of a first person and the resolution of the image 49 including the iris 47 and the pupil 48 of a second person can differ from each other.

The data 62 is the size of the pupil at Time n. That is, the data 62 is the size of the pupil at a time after the time when the size of the pupil included in the data 61 is measured. Note that in the case where the data 61 is the change over time in the ratio between the size of the pupil and the size of the iris, the data 62 is also the ratio between the size of the pupil and the size of the iris.

FIG. 7A2 is a diagram showing an example of the relation between the pupil diameter and the time. In FIG. 7A2, a black circle represents an actual measured value of the pupil diameter. Also in the other diagrams, an actual measured value is represented by a black circle in some cases. As shown in FIG. 7A2, the data 62 can be the size of the pupil at the time after the time when the size of the pupil included in the data 61 is measured. For example, the data 62 can be the size of the pupil at a time subsequent to the time when the size of the pupil included in the data 61 is measured last.

Here, in the case where a function of presuming whether there is fatigue is imparted to the generator 60, a change over time in the size of a pupil of a person who has fatigue is not included in the data 61 or the data 62. That is, the data 61 is a change over time in the size of a pupil of a person who has no fatigue, and the data 62 is the size of the pupil of the person who has no fatigue. In the case where a function of presuming whether there is drowsiness is imparted to the generator 60, a change over time in the size of a pupil of a person who has drowsiness is included in neither the data 61 nor the data 62. That is, the data 61 is a change over time in the size of a pupil of a person who does not have drowsiness, and the data 62 is the size of a pupil of a person who has no drowsiness.

The learning of the generator 60 is performed so that output data can become closer to the data 62 when the data 61 is input to the generator 60. That is, the learning of the generator 60 is performed using the data 62 as correct data. By the learning of the generator 60, the generator 60 generates a learning result 63. In the case where a neural network is used as the generator 60, the learning result 63 can be a weighting coefficient or the like.

FIG. 7B1 and FIG. 7B2 are schematic views illustrating Step S15 and show an example of the method for presuming fatigue, drowsiness, or the like of the user of the information terminal provided with the information processor 30, with the use of the generator 60. In Step S15, first, as illustrated in FIG. 7B1, data 64 indicating the change over time in the size of the pupil, which is obtained in Step S14, is input to the generator 60 in which the learning result 63 has been read. For example, in the case where the change over time in the size of the pupil from Time 1 to n−1 are used as the input data at the time of the learning of the generator 60 in Step S05, the change over time in the size of the pupil from Time 1 to n−1 are also used as input data at the time of an inference in Step S15. That is, the data 64 is a change over time in the size of the pupil of the user of the information terminal provided with the information processor 30 from Time 1 to n−1. Thus, the generator 60 performs inference on the data 64 to output data 65. Note that, furthermore, data from Time 2 to n is used as input data and data at Time n+1 may be inferred with the use of the data 65 that is the inference data at Time n.

Note that in the case where the data 61 is the change over time in the ratio between the size of the pupil and the size of the iris, the data 64 is also a change over time in the ratio between the size of the pupil and the size of the iris. When the data 64 is the change over time in the ratio between the size of the pupil and the size of the iris, the resolutions of the images 49 including the iris 47 and the pupil 48 can differ from each other, for example, in the case of detecting the pupil by a method shown in Step S37. For example, the resolution of the image 49 which the arithmetic unit obtains in order to calculate the ratio between the size of the pupil 48 and the size of the iris 47 at Time 1 can be different from the resolution of the image 49 which the arithmetic unit obtains in order to calculate the ratio between the size of the pupil 48 and the size of the iris 47 at Time n−1.

The data 65 is an estimated value of the size of the pupil at a time after the time when the size of the pupil included in the data 64 is measured, which is obtained by the calculation by performing inference on the data 64 on the basis of the learning result 63. For example, in the case where the data 64 is a change over time in the size of the pupil from Time 1 to n−1, the data 65 can be the size of the pupil at Time n. In FIG. 7B1, the actual measured values of the size of the pupil from Time 1 to n−1 are represented as $x_1$ to $x_{n-1}$, respectively. In addition, an estimated value of the size of the pupil at Time n is represented as $x_n(E)$. Note that in the case where the data 64 is the change over time in the ratio between the size of the pupil and the size of the iris, the data 65 is the ratio between the size of the pupil and the size of the iris.

Next, as illustrated in FIG. 7B2, data 66 that represents the actual measured value of the size of the pupil at, for example, Time n and the data 65 that is the data output from the generator 60 are compared with each other. In other words, for example, the actual measured value at Time n and the estimated value are compared with each other. With the comparison result, whether there is fatigue, drowsiness, or the like is presumed. For example, in the case where the generator 60 has a function of presuming whether there is fatigue, the learning of the generator 60 is performed with the use of a change over time in the size of a pupil of a person who has no fatigue, as input data, for example. Accordingly, when the user of the information terminal provided with the information processor 30 is in a state without fatigue, the data 65 becomes close to the data 66. That is, a difference between the data 65 and the data 66 becomes small. In contrast, when the user of the information terminal provided with the information processor 30 is in a state with fatigue, the difference between the data 66 and the data 65 becomes larger than that in the case where the user of the information terminal provided with the information processor 30 is in the state without fatigue. From the above, the comparison between the data 66 and the data 65 makes it possible to presume whether the user of the information terminal provided with the information processor 30 has fatigue. The same applies to the case of presuming whether there is drowsiness. Note that in the case where the data 65 is an estimated value of the ratio between the size of the pupil and the size of the iris, the data 66 is an actual measured value of the ratio between the size of the pupil and the size of the iris.

The function of the generator 60 can be imparted to both the arithmetic unit 23 and the arithmetic unit 33. In this case, the arithmetic unit 23 included in the information processor 20 can generate the learning result 63 by performing the learning of the generator 60, and the learning result 63 can be supplied from the information processor 20 to the information processor 30. Thus, even without learning, the arithmetic unit 33 provided in the information processor 30 can perform inference on the data input to the arithmetic unit 33, on the basis of the learning result by the arithmetic unit 23 provided in the information processor 20. Accordingly, the arithmetic processing performance of the arithmetic unit 33 can be lower than that of the arithmetic unit 23. Note that the learning result 63 can be stored in the auxiliary memory unit 25 and the auxiliary memory unit 35.

[Example_2 of Method for Presuming Fatigue, Drowsiness, or the Like]

Figure 8A:
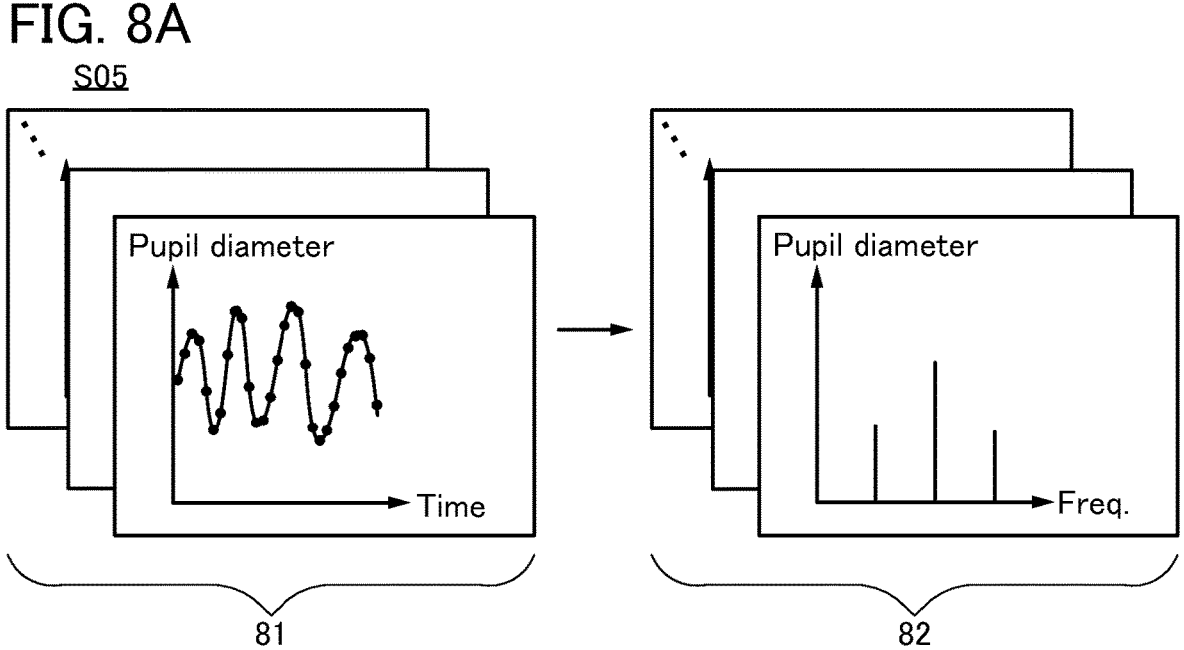
FIG. 8A and FIG. 8B are schematic views illustrating an example of a method for operating the information processor.
Figure 8B:
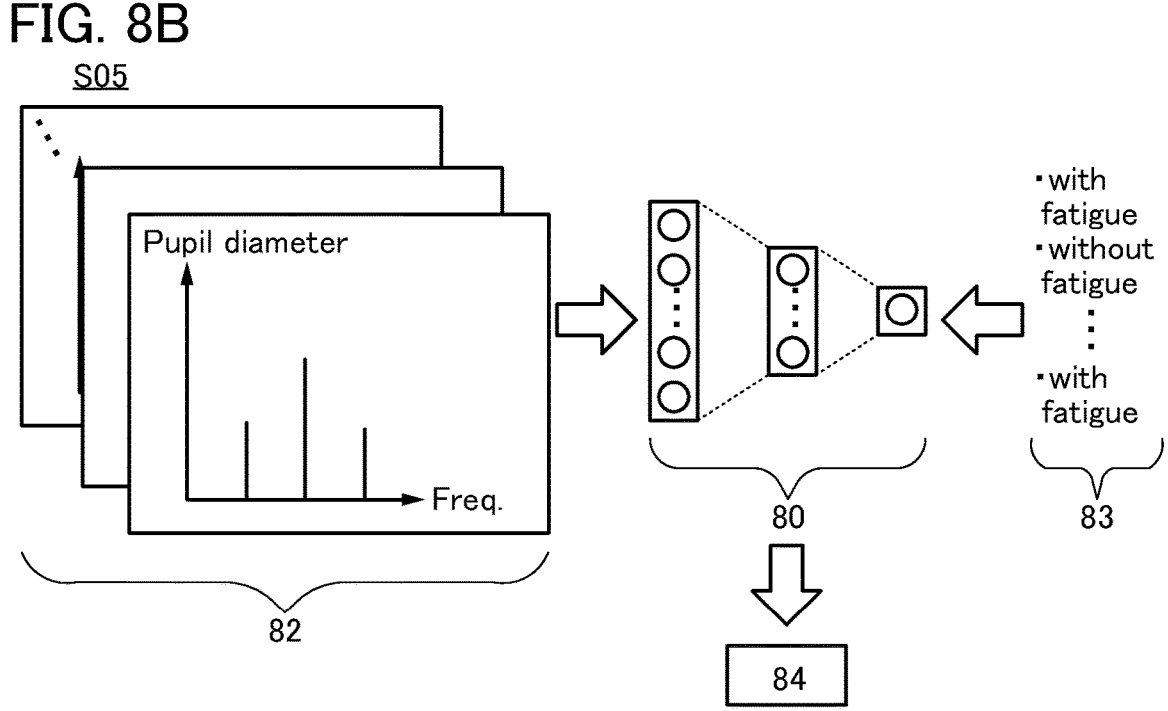

FIG. 8A and FIG. 8B are schematic views illustrating Step S05 and show an example of a learning method of a generator, which is different from the above method. Specifically, FIG. 8A illustrates an example of a method for generating data input to a generator as learning data, and FIG. 8B illustrates an example of a learning method of a generator 80. The generator 80 is a program that performs arithmetic operation by machine learning. For example, a neural network can be used as the generator 80.

Data 81 shown in FIG. 8A is data obtained in Step S04 and can be a change over time in the size of a pupil. As described above, for example, in the case where the pupil is detected by circular extraction, the radius or diameter of the pupil can be regarded as the size of the pupil. In addition, in the case where the pupil is extracted as an elliptical shape, the length of the major axis and the length of the minor axis can be regarded as the size of the pupil. Moreover, the area of the pupil can be regarded as the size of the pupil. As in the learning method shown in FIG. 7A1, the data 81 can be a change over time in the ratio between the size of the pupil and the size of an iris.

Here, the data 81 is subjected to Fourier transform to generate data 82. As shown in FIG. 8A, the change over time in the pupil diameter can be converted into frequency characteristics of the pupil diameter by the Fourier transform. Note that in the case where the data 81 is a change over time in the ratio between the size of the pupil and the size of the iris, the data 82 can be frequency characteristics of the ratio between the size of the pupil and the size of the iris.

The learning of the generator 80 can be performed using the data 82 and data 83 as illustrated in FIG. 8B. The data 82 represents the frequency characteristics of the pupil diameter as described above. The data 83 can be a label indicating whether there is fatigue. For example, frequency characteristics of the size of a pupil of a person who has fatigue and frequency characteristics of the size of a pupil of a person who has no fatigue are made to be both included as the data 83. Then, the frequency characteristics of the size of the pupil of the person who has fatigue is linked with a label "with fatigue" and the frequency characteristics of the size of the pupil of the person who has no fatigue is linked with a label "without fatigue." The data 83 may be a label indicating whether there is drowsiness.

The learning of the generator 80 is performed so that output data can become closer to the data 83 when the data 82 is input to the generator 80. That is, the learning of the generator 80 is performed using the data 83 as correct data. By the learning of the generator 80, the generator 80 generates a learning result 84. In the case a neural network is used as the generator 80, the learning result 84 can be a weighting coefficient or the like.

The change over time in the size of the pupil is subjected to Fourier transform, whereby the data input to the generator 80 can become data that is not time series data. Therefore, the generator 80 can perform learning and inference without using an RNN as the generator 80.

Figure 9A:
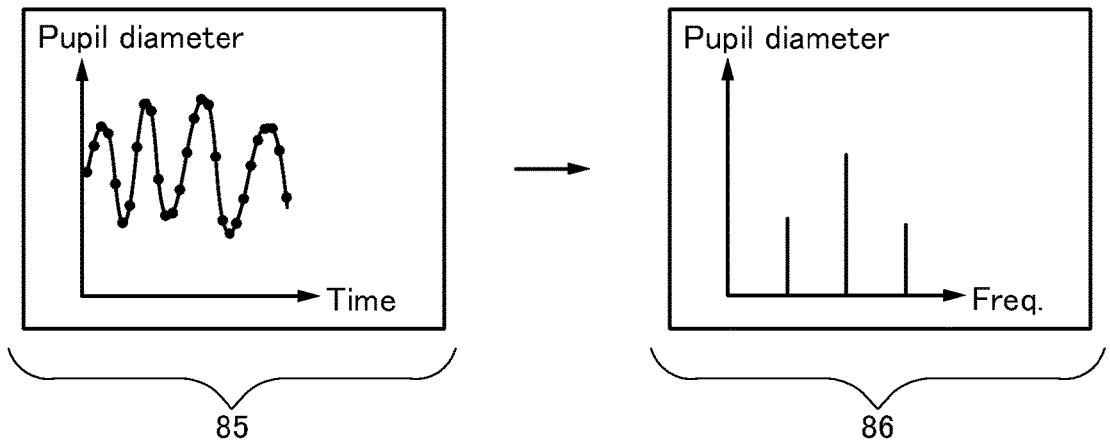
FIG. 9A and FIG. 9B are schematic views illustrating an example of a method for operating the information processor.
Figure 9B:
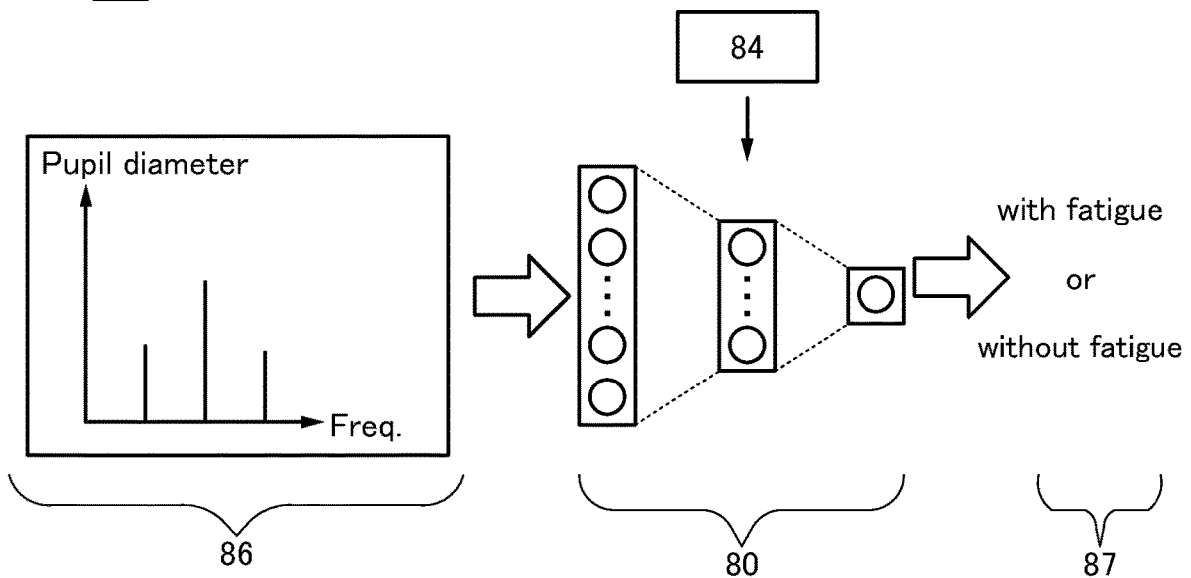

FIG. 9A and FIG. 9B are schematic views illustrating Step S15 and show an example of the method for presuming fatigue, drowsiness, or the like of the user of the information terminal provided with the information processor 30, with the use of the generator 80.

Data 85 shown in FIG. 9A is data obtained in Step S04 and can be a change over time in the size of the pupil. As described above, when the pupil is detected by, for example, circular extraction, the radius or diameter of the pupil can be regarded as the size of the pupil. In addition, in the case where the pupil is extracted as an elliptical shape, the length of the major axis and the length of the minor axis can be regarded as the size of the pupil. Moreover, the area of the pupil can be regarded as the size of the pupil. Note that in the case where the data 81 shown in FIG. 8A is a change over time in the ratio between the size of the pupil and the size of the iris, the data 85 is also a change over time in the ratio between the size of the pupil and the size of the iris.

Here, the data 85 is subjected to Fourier transform to generate data 86. As shown in FIG. 9A, the change over time in the pupil diameter can be converted into frequency characteristics of the pupil diameter by Fourier transform. Note that in the case where the data 85 is a change over time in the ratio between the size of the pupil and the size of the iris, the data 86 can be frequency characteristics of the ratio between the size of the pupil and the size of the iris.

Then, as shown in FIG. 9B, the data 86 after Fourier transform is input to the generator 80. Thus, the generator 80 can perform inference on the data 86 and output data 87 indicating whether there is fatigue. Note that in the case where the data 87 shown in FIG. 9B is a label indicating whether there is drowsiness, the data 87 output by the generator 80 can be data indicating whether there is drowsiness.

As in the case of the function of the generator 60 and the function of a generator 70, the function of the generator 80 can be imparted to both the arithmetic unit 23 and the arithmetic unit 33. Thus, the arithmetic processing performance of the arithmetic unit 33 can be lower than that of the arithmetic unit 23.

[Example_3 of Method for Presuming Fatigue, Drowsiness, or the Like]

FIG. 10A is a schematic view illustrating Step S05 and shows an example of a learning method of a generator, which is different from the above method. In FIG. 10A, learning of the generator 70 is performed. The generator 70 is a program that performs arithmetic operation by machine learning. For example, a neural network can be used as the generator 70; for example, an autoencoder can be used.

When the generator 70 performs learning, data 71 is input to the generator 70. The data 71 is data obtained in Step S04 and can be a change over time in the size of a pupil. Here, in the case where a function of presuming whether there is fatigue is imparted to the generator 70, a change over time in the size of a pupil of a person who has fatigue is not included in the data 71. That is, the data 71 is a change over time in the size of a pupil of a person who has no fatigue. In the case where a function of presuming whether there is drowsiness is imparted to the generator 70, a change over time in the size of a pupil of a person who has drowsiness is not included in the data 71. That is, the data 71 is a change over time in the size of a pupil of a person who has no drowsiness.

As described above, for example, in the case where the pupil is detected by circular extraction, the radius or diameter of the pupil can be regarded as the size of the pupil. In addition, in the case where the pupil is extracted as an elliptical shape, the length of the major axis and the length of the minor axis can be regarded as the size of the pupil. Moreover, the area of the pupil can be regarded as the size of the pupil.

As in the learning method shown in FIG. 7A1, the data 71 can be a change over time in the ratio between the size of the pupil and the size of the iris. As in the case shown in FIG. 8A, a change over time in the size of the pupil that has been subjected to Fourier transform may be used as the data 71.

The learning of the generator 70 is performed so that data 72 that is output data can become closer to the input data 71 when the data 71 is input to the generator 70. That is, the learning of the generator 70 is performed so that the data 71 and the data 72 can be equal to each other. By the learning of the generator 70, the generator 70 generates a learning result 73. In the case a neural network is used as the generator 70, the learning result 73 can be a weighting coefficient or the like.

FIG. 10B1 and FIG. 10B2 are schematic views illustrating Step S15 and show an example of the method for presuming fatigue, drowsiness, or the like of the user of the information terminal provided with the information processor 30, with the use of the generator 70. In Step S15, first, as illustrated in FIG. 10B1, data 74 indicating a change over time in the size of the pupil obtained in Step S14 is input to the generator 70 to which the learning result 73 is read. Thus, the generator 70 performs inference on the data 74 to output data 75.

Note that in the case where the data 71 is the change over time in the ratio between the size of the pupil and the size of the iris, the data 74 is also a change over time in the ratio between the size of the pupil and the size of the iris. In the case where data after Fourier transform is used as the data 71, data after Fourier transform is also used as the data 74. For example, in the case where the data 71 is a change over time in the size of the pupil that has been subjected to Fourier transform, the data 74 is also a change over time in the pupil that has been subjected to Fourier transform.

Next, as illustrated in FIG. 10B2, the data 74 that is the data input to the generator 70 and the data 75 that is the data output from the generator 70 are compared with each other. With the comparison result, whether there is fatigue, drowsiness, or the like is presumed. For example, in the case where the generator 70 has a function of presuming whether there is fatigue, the learning of the generator 70 is performed with the use of a change over time in the size of a pupil of a person who has no fatigue, as input data, for example. Accordingly, when the user of the information terminal provided with the information processor 30 is in a state without fatigue, the data 75 that is the output data from the generator 70 becomes close to the data 74 that is the input data to the generator 70. That is, a difference between the data 74 and the data 75 becomes small. In contrast, when the user of the information terminal provided with the information processor 30 is in a state with fatigue, the difference between the data 74 and the data 75 becomes larger than that in the case where the user of the information terminal provided with the information processor 30 is in the state without fatigue. From the above, the comparison between the data 74 and the data 75 makes it possible to presume whether the user of the information terminal provided with the information processor 30 has fatigue. The same applies to the case of presuming whether there is drowsiness.

As in the case of the function of the generator 60, the function of the generator 70 can be imparted to both the arithmetic unit 23 and the arithmetic unit 33. Thus, the arithmetic processing performance of the arithmetic unit 33 can be lower than that of the arithmetic unit 23.

[Example_4 of Method for Presuming Fatigue, Drowsiness, or the Like]

Figure 11:
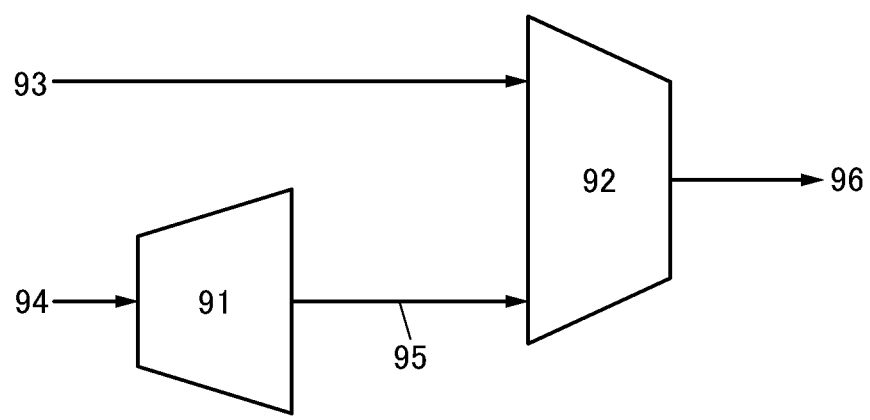
FIG. 11 is a diagram showing AnoGAN, which can be applied to one embodiment of the present invention.

The learning performed in Step S05 and the inference performed in Step S15 on the basis of the learning result may be performed using a generative adversarial network (GAN). They may be performed using AnoGAN (Anormaly GAN), for example. FIG. 11 illustrates AnoGAN that enables the above learning and inference.

The AnoGAN illustrated in FIG. 11 includes a generator 91 and a discriminator 92. The generator 91 and the discriminator 92 can be formed with a network.

Data 93 that is time-series data representing a change over time in the size of a pupil of a person who has no fatigue, drowsiness, or the like and is obtained by image capturing is input to the discriminator 92. Alternatively, data 95 that is time-series data generated by the generator 91 to which data 94 is input is input to the discriminator 92. The discriminator 92 has a function of making a determination (also referred to as an authenticity determination) whether the input data is the data 93 obtained by image capturing or the data 95 generated by the generator 91. Note that the data 93 may be data obtained in such a manner that the time-series data that represents a change over time in the size of a pupil of a person who has no fatigue, drowsiness, or the like and is obtained by image capturing is subjected to Fourier transform.

The determination result is output as data 96. The data 96 can be continuous values between 0 and 1, for example. In this case, for example, the discriminator 92 outputs a value close to 1 as the data 96 in the case where data input after the termination of the learning is the data 93 obtained by image capturing and outputs a value close to 0 as the data 96 in the case where the input data is the data 95 generated by the generator 91.

The data 94 is multi-dimensional random numbers (also referred to as a latent variable). Here, the latent variable represented by the data 94 is referred to as a latent variable z. The generator 91 has a function of generating data that is as close as possible to the data representing a change over time in the size of the pupil of the person who has no fatigue, drowsiness, or the like, on the basis of such data 94.

As for the learning, the learning of the discriminator 92 and the learning of the generator 91 are performed alternately. That is, the weighting coefficient of the neural network forming the generator 91 is fixed at the time of the learning of the discriminator 92. In addition, the weighting coefficient of the neural network forming the discriminator 92 is fixed at the time of the learning of the generator 91.

The data 93 obtained by image capturing or the data 95 generated by the generator 91 is input to the discriminator 92 at the time of the learning of the discriminator 92. A correct label is given to the data input to the discriminator 92. The correct label for the data 96 output by the discriminator 92 can be determined in the following manner. For example, the correct label is "1" when the data 93 is input to the discriminator 92, and the correct label is "0" when the data 95 is input to the discriminator 92. The learning performed by the above method enables the discriminator 92 to make an authenticity determination.

The data 94 representing the latent variable z is input to the generator 91 at the time of the learning of the generator 91. Then, the generator 91 generates the data 95 on the basis of the input data 94. A correct label of the data 96 is "1". Then, the learning of the generator 91 is performed so that the value of the data 96 output from the discriminator 92 can be "1". As the learning of the generator 91 advances, the generator 91 becomes able to generate data similar to the data 93 obtained by image capturing, as the data 95.

After the completion of the learning of the generator 91, the generator 91 becomes able to generate the data 95 similar to the data 93 obtained by image capturing even when any latent variable z is input as the data 94.

Next, operation at the time of inference is described.

First, data representing a change over time in the size of a pupil of a person who has no fatigue, drowsiness, or the like is obtained by picture taking. At this time, a space of a latent variable is searched, and a latent variable z1 generating data that is the most similar to the data of the size of the pupil of the person who has no fatigue, drowsiness, or the like is found by a gradient descent method or the like. The generator is 91 and has a function of generating data extremely similar to the data representing a change over time in the size of the pupil of the person who has no fatigue, drowsiness, or the like by learning. Thus, data generated from the latent variable z1 by the generator and the data representing a change over time in the size of the pupil of the person who has no fatigue, drowsiness, or the like are extremely similar to each other.

Next, data representing a change over time in the size of a pupil of a person who has fatigue, drowsiness, or the like is obtained by image capturing. At this time, the space of the latent variable is searched, and a latent variable z2 generating data that is the closest to the data representing a change over time in the size of the pupil of the person who has fatigue, drowsiness, or the like is found by a gradient descent method or the like. The generator 91 has a capability of generating data extremely close to the data representing a change over time in the size of the pupil of the person who has no fatigue, drowsiness, or the like but does not have a capability of generating data similar to the data representing a change over time in the size of the pupil of the person who has fatigue, drowsiness, or the like. Therefore, the data generated from the latent variable z2 by the generator and the data obtained by picture taking and representing a change over time in the size of the pupil of the person who has fatigue, drowsiness, or the like are not extremely similar to each other. From the above, whether there is fatigue, drowsiness, or the like can be presumed by the generator 91.

As described above, as shown in FIG. 7 to FIG. 11, the information processor 30 presumes fatigue, drowsiness, or the like of the user of the information terminal provided with the information processor 30 by arithmetic operation using machine learning. With the use of machine learning, it is possible to presume fatigue, drowsiness, or the like with high accuracy even when, for example, a change over time in a feature value in the case of presuming that there is fatigue and a change over time in a feature value in the case of presuming that there is no fatigue are not set manually. Specifically, it is possible to presume fatigue, drowsiness, or the like with high accuracy even when, for example, a change over time in the size of the pupil in the case of presuming that there is fatigue and a change over time in the size of the pupil in the case of presuming that there is no fatigue are not set manually. In addition, fatigue, drowsiness, or the like can be presumed by a simple method because it is possible to presume fatigue, drowsiness, or the like even when, for example, a change over time in a feature value in the case of presuming that there is fatigue and a change over time in a feature value in the case of presuming that there is no fatigue are not set manually.

An alarm indicating that fatigue, drowsiness or the like is generated can be displayed, for example, on a display portion of the information terminal provided with the information processor 30 when the information processor 30 presumes that there is fatigue, drowsiness, or the like. Accordingly, it becomes possible to urge the user of the information terminal to stop the use of the information terminal early, for example. Alternatively, the information terminal provided with the information processor 30 can be turned off. Therefore, it is possible to inhibit health hazards that are caused when the user of the information terminal continues using the information terminal even though fatigue, drowsiness, or the like is caused in the user.

REFERENCE NUMERALS

10: information processing system, 20: information processor, 21: imaging unit, 22: display unit, 23: arithmetic unit, 24: main memory unit, 25: auxiliary memory unit, 26: communication unit, 27: transmission path, 30: information processor, 31: imaging unit, 32: display unit, 33: arithmetic unit, 34: main memory unit, 35: auxiliary memory unit, 36: communication unit, 37: transmission path, 41: image, 42: image, 43: image, 44: image, 45: image, 46: image, 47: iris, 48: pupil, 49: image, 50: generator, 51: data, 52: data, 53: learning result, 57: iris, 58: pupil, 59: image, 60: generator, 61: data, 62: data, 63: learning result, 64: data, 65: data, 66: data, 70: generator, 71: data, 72: data, 73: learning result, 74: data, 75: data, 80: generator, 81: data, 82: data, 83: data, 84: learning result, 85: data, 86: data, 87: data, 91: generator, 92: discriminator, 93: data, 94: data, 95: data, 96: data

The invention claimed is:

1. An information processor comprising: a display unit; an imaging unit; and an arithmetic unit, wherein the arithmetic unit has a neural network system learned by a brightness of an environment, lengths of a major axis and a minor axis of each pupil, and change cycles of the lengths of a person in a first moving image, wherein the person in the first moving image is a person who has no fatigue, wherein the imaging unit is configured to obtain a second moving image comprising data on a face of a user of the information processor, wherein the arithmetic unit is configured to detect eyes of the user in the second moving image, wherein the arithmetic unit is configured to detect a pupil from each of the detected eyes, wherein the arithmetic unit is configured to calculate a length of a major axis and a length of a minor axis of each of the detected pupils, wherein the information processor is configured to infer a level of fatigue of the user based on the neural network system, wherein, when the information processor infers that the user is fatigued, the information processor is configured to display an alarm indicating that the user is fatigued on the display unit, and wherein a presence or an absence of the fatigue of the user in the second moving image is inferred from the brightness of the environment, the lengths of the major axis and the minor axis of the pupils, and change cycles of the lengths in the second moving image based on a learning result of the neural network system by the first moving image.

2. An information processor comprising: an imaging unit; and an arithmetic unit, wherein the arithmetic unit has a neural network system learned by a brightness of an environment, lengths of a major axis and a minor axis of each pupil, and change cycles of the lengths of a person in each of two or more first moving images, wherein the person in each of the two or more first moving images is a person who has no fatigue, wherein the imaging unit is configured to obtain a second moving image comprising data on a face of a user of the information processor, wherein the arithmetic unit is configured to detect each eye of the user in the second moving image, wherein the arithmetic unit is configured to detect a pupil from each of the detected eyes, wherein the arithmetic unit is configured to calculate a length of a major axis and a length of a minor axis of each of the detected pupils, wherein the information processor is configured to infer a level of fatigue of the user in the second moving image based on the neural network system, wherein, when the information processor infers that the user is fatigued, the information processor is configured to be turned off, and wherein a presence or an absence of the fatigue of the user in the second moving image is inferred from the brightness of the environment, the lengths of the major axis and the minor axis of the pupils, and change cycles of the lengths in the second moving image based on a learning result of the neural network system by the two or more first moving images.

3. An information processor, wherein the information processor has a neural network system learned by a brightness of an environment, lengths of a major axis and a minor axis of each pupil, and change cycles of the lengths of two or more first moving images and two or more second moving images, wherein each of the two or more first moving images comprises data on a face of a user who has no fatigue under various brightness levels of an environment, wherein each of the two or more second moving images comprises data on a face of a user who has fatigue under various brightness levels of an environment, wherein the information processor is configured to obtain a third moving image, wherein the information processor is configured to detect each eye from the third moving image, wherein the information processor is configured to detect a pupil from each of the detected eyes, wherein the information processor is configured to calculate a length of a major axis and a length of a minor axis of each of the detected pupils, wherein the information processor is configured to infer a level of fatigue of the user in the third moving image based on the neural network system, wherein, when the information processor infers that the user in the third moving image is fatigued, the information processor is configured to either display an alarm indicating that the user is fatigued on a display unit included in the information processor or to turn off power supply to the information processor, and wherein a presence or an absence of the fatigue of the user is inferred from the brightness of the environment, the lengths of the major axis and the minor axis of the pupils, and change cycles of the lengths in the third moving image based on a learning result of the neural network system by the two or more first moving images and two or more second moving images.

* * * * *